United States Patent [19]

DeLuca et al.

[11] Patent Number: 4,461,766

[45] Date of Patent: Jul. 24, 1984

[54] METHOD FOR INDUCING MOLTING IN LAYING HENS

[75] Inventors: Hector F. DeLuca; Heinrich K. Schnoes; Leslie E. Hart, all of Madison, Wis.

[73] Assignee: Wisconsin Alumni Research Foundation, Madison, Wis.

[21] Appl. No.: 479,293

[22] Filed: Mar. 28, 1983

[51] Int. Cl.$^3$ .............................................. A61K 31/59
[52] U.S. Cl. ................................................... 424/236
[58] Field of Search ......................................... 424/236

[56] References Cited

PUBLICATIONS

Chem. Abstracts, vol. 96 (1982), Par. 33740(b).

*Primary Examiner*—Elbert L. Roberts
*Attorney, Agent, or Firm*—Howard W. Bremer

[57] ABSTRACT

The invention provides a method for inducing molting in egg-laying hens as a means for extending their productive egg-laying life by administering to the hens an effective amount of a side chain-hydroxylated vitamin $D_3$ compound.

3 Claims, No Drawings

METHOD FOR INDUCING MOLTING IN LAYING HENS

This invention was made with Government support under NIH Grant No. AM14881 awarded by the Department of Health and Human Services. The Government has certain rights in this invention.

TECHNICAL FIELD

This invention relates to a method for extending the useful egg-laying life of hens.

More particularly this invention relates to a method for inducing molting in egg-laying hens as a means of extending their useful egg-laying life.

Still more particularly this invention relates to a method for inducing molting in egg-laying hens by administering to them particular vitamin D derivatives.

BACKGROUND

As egg-laying hens age the eggs which they lay, although becoming larger in size, exhibit a progressive decrease in eggshell thickness. Ultimately, the eggs are characterized by such thin shells that the loss due to breakage makes it uneconomical to maintain the hens for their egg production since the cost of the feed becomes greater than the number of marketable eggs produced. This pattern generally is found to occur after at least one year of egg production. Two procedures, appear to be available to address this problem, both of which are quite drastic: (1) the hens can be sacrificed and used as a food source; or (2) or the hens can be induced to molt. Molting can be induced either by starving the hens for a period of time or by withdrawing from their diet an essential nutrient which will bring about a loss in weight. Then, about eight weeks after molting, the hens are returned to egg-laying productivity. The eggs produced after molting tend to be smaller in size than before molting and have thicker shells. By this means the hens are returned to egg production on an economically sound basis for perhaps an additional year. As mentioned above, either of these treatments is considered rather drastic since hens subjected to such treatment must first recover their weight and health before they again are productive and a percentage of hens subjected to such treatment do not survive. Also, it is impractical to treat hens en masse by either of such procedures.

DISCLOSURE OF THE INVENTION

To support calcium and phosphorus metabolism in the hen, vitamin D is required. Vitamin D must first be hydroxylated on carbon-25 and subsequently in the kidney on carbon-1 to produce the active hormone, 1,25-dihydroxyvitamin $D_3$. This hormone functions in intestine, bone, kidney and shell gland to promote calcium movements required for life, health and egg formation in the hen. It is also known that 25-hydroxyvitamin $D_3$ undergoes a variety of conversions to other metabolites. Of particular importance is 24,25-dihydroxyvitamin $D_3$, a metabolite that is formed in large amounts, particularly when the active hormone 1,25-dihydroxyvitamin $D_3$ is not made under physiologic circumstances. When calcium is needed, the kidney converts 25-hydroxyvitamin $D_3$ to predominantly 1,25-dihydroxyvitamin $D_3$. However, when calcium is not needed, 25-hydroxyvitamin $D_3$ is converted to 24,25-dihydroxyvitamin $D_3$. Although the function of 1,25-dihydroxyvitamin $D_3$ is known, at the present time there is no uniform agreement on the possible role of 24,25-dihydroxyvitamin $D_3$ in biological systems.

It has now been found that 24,25-dihydroxyvitamin $D_3$ when used as a replacement for vitamin D in the diet of laying hens induces molting. The molting cycle is rapid and, subsequent to molting, the hens quickly return to normal egg production.

It is also well known that in situations when calcium is not required in the animal metabolic process, vitamin D is converted to other side chain modified derivatives, for example, 25-hydroxyvitamin $D_3$-26,23-lactone, 25,26-dihydroxyvitamin $D_3$, 23,25-dihydroxyvitamin $D_3$ and their 1-hydroxylated analogs. It would, therefore, appear that the side chain modified derivatives, and particularly the side chain-hydroxylated derivatives of 25-hydroxylated vitamin $D_3$ could play an important role in inducing physiologic molting in the hen and other avian species.

DESCRIPTION OF THE INVENTION

Leghorn pullets were raised to maturity with 25-hydroxyvitamin $D_3$ as their source of vitamin D. When they began producing normal numbers of eggs having high quality shells and hatchability, they were placed on a diet containing 3% calcium and 15% protein. The composition of the diet is given in the following table.

| Diet for Laying Hens (g/1.04 kg diet) | | | |
|---|---|---|---|
| sucrose | 492.00 | Trace Salt | 6.6 |
| 44% soyprotein | 341.0 | $MgSO_4$ | 3.897 |
| $CaCO_3$ | 70.7 | $MnSO_4$ | 0.391 |
| Wesson Oil | 40.0 | KI | 0.062 |
| $KH_2PO_4$ | 15.5 | $CuSO_4$ | 0.015 |
| $CaHPO_4.2H_2O$ | 11.3 | ZnO | 0.055 |
| NaCl (iodized) | 8.0 | Na molybdate | 0.031 |
| Solka Floc | 1.5 | | |
| Premix | 53.3 | Na selenite | 0.002 |
| Methionine | 5.97 | Ferric citrate | 2.148 |
| Glycine | 3.98 | | |
| Choline chloride | 2.29 | | |
| α-tocopherol acetate | 0.20 | | |
| retinyl acetate | .009 | | |
| menadione | .0015 | | |
| sucrose | 38.72 | | |
| Vitamin-mix | 2.13 | | |
| Thiamine | .006 | | |
| Riboflavin | .009 | | |
| Pantothenic acid | .020 | | |
| Niacin | .050 | | |
| Pyridoxine | .008 | | |
| Biotin | .0003 | | |
| Insitol | 1.007 | | |
| Folic Acid | .002 | | |
| Vitamin $D_{12}$ (.1% in mannitol) | .020 | | |
| Sucrose | 1.007 | | |

After 6 weeks, 5 hens were given 2 μg/day of 24.25-dihydroxyvitamin $D_3$ orally in 0.5 ml of Wesson oil. Another group of 5 hens was given 25-hydroxyvitamin $D_3$ at the same concentration while still another group was given 1,25-dihydroxyvitamin $D_3$ at 400 nanograms per day. Hens given the 24,25-dihydroxyvitamin $D_3$ began molting after initiation of the compound. No hen in any of the other groups went into the molting cycle. Subsequent to molting the hens went back into normal egg production. Preferably during this period of normal production the 24,25-dihydroxyvitamin $D_3$ is replaced by a vitamin D compound, for example, by 2-8 μg per kilogram of diet of 25-hydroxyvitamin $D_3$, or by vitamin $D_3$ at 12 μg/kg of diet. Additionally, the vitamin D derivatives, 1α-hydroxyvitamin $D_3$ and 1,25-dihydroxyvitamin $D_3$ can be substituted for the vitamin $D_3$ or 25-hydroxyvitamin $D_3$ in amounts suitable to the promotion of normal egg production.

It is evident from the foregoing that 24,25-dihydroxyvitamin $D_3$ can be substituted for vitamin D in the diet of hens to induce molting and that the molting hens can be brought back into production, preferably by replacement of the 24,25-dihydroxyvitamin $D_3$ with vitamin $D_3$, 25-hydroxyvitamin $D_3$ or a 1-hydroxylated form of those vitamins $D_3$ derivatives. Such procedure will undoubtedly be much less traumatic to the hens than the starvation method heretofore utilized to induce molting. Moreover, there will be fewer losses of birds and the hens should be better able to return to their original laying capacity. In addition, the use of a diet so modified is a practical method for inducing, maintaining and terminating molting according to the desires of the producer.

It is anticipated that 2 μg/day of 24,25-dihydroxyvitamin $D_3$ is the minimal dose which will induce molting. Larger amounts, such as 200 μg/bird/day and up to as high as 1000 μg/bird/day can be given with no adverse effects. It is anticipated that if a bird is not depleted of vitamin D larger amounts of 24,25-dihydroxyvitamin $D_3$ will be required to induce molting. In any circumstance, however, the amount of 24,25-dihydroxyvitamin $D_3$ should be sufficient to induce molting. Amounts in excess of such level should be avoided as being economically unsound.

The molting inducing compounds can be administered in any convenient manner and most advantageously as a feed supplement in the diet of the birds. Thus, the compounds can be dispersed in a suitable edible oil, e.g. corn oil, soybean oil, cottonseed oil, and dispersed in the feed or can also be so dispersed in solid form, e.g. crystalline or amorphous form in a solid edible inert carrier as is well known in the art.

We claim:

1. A method for inducing molting in birds which comprises administering to the birds 24,25-dihydroxyvitamin $D_3$ in an amount from about 2 to about 1000 micrograms per day and sufficient to induce molting.

2. A method for extending the productive lives of egg-laying hens which comprises, in sequence, replacing the vitamin D compound in the normal diet of the hens with 24,25-dihydroxyvitamin $D_3$ in an amount sufficient to insure that the hens will receive from about 2 to about 1000 micrograms of said 24,25-dihydroxyvitamin $D_3$ per day feeding the thus altered diet to said hens until molting occurs after molting has occurred replacing said 24,25-dihydroxyvitamin $D_3$ in the hen's diet with a compound selected from the group consisting of vitamin $D_3$, 25-hydroxyvitamin $D_3$, 1α-hydroxyvitamin $D_3$, 1,25-dihydroxyvitamin $D_3$ and mixtures thereof and feeding the 24,25-dihydroxyvitamin $D_3$-free diet to the hens whereby the production of normal eggs by the hens is reestablished.

3. The method of claim 2 wherein the 24,25-dihydroxyvitamin $D_3$ is included in the diet of the hens in an amount from about 20 μg/kg of diet to about 10 μg/kg of diet.

* * * * *